United States Patent
Zhao et al.

(10) Patent No.: US 10,197,516 B2
(45) Date of Patent: Feb. 5, 2019

(54) NON-CONTACT QUALITY CONTROL OF FIBER COMPOSITES

(71) Applicant: Ford Global Technologies, LLC, Dearborn, MI (US)

(72) Inventors: Haibo Zhao, Northville, MI (US); Qian Zhou, Northville, MI (US)

(73) Assignee: Ford Global Technologies, LLC, Dearborn, MI (US)

(*) Notice: Subject to any disclaimer, the term of this patent is extended or adjusted under 35 U.S.C. 154(b) by 241 days.

(21) Appl. No.: 15/093,307

(22) Filed: Apr. 7, 2016

(65) Prior Publication Data

US 2017/0292925 A1  Oct. 12, 2017

(51) Int. Cl.
| | |
|---|---|
| G01N 25/20 | (2006.01) |
| G01N 33/36 | (2006.01) |
| H05B 6/10 | (2006.01) |

(52) U.S. Cl.
CPC .......... *G01N 25/20* (2013.01); *G01N 33/367* (2013.01); *H05B 6/10* (2013.01)

(58) Field of Classification Search
CPC ......... G01N 33/367; G01N 25/20; H05B 6/10
USPC .............................................. 374/45, E7.001
See application file for complete search history.

(56) References Cited

U.S. PATENT DOCUMENTS

| | | |
|---|---|---|
| 5,089,700 A | 2/1992 | Sapia et al. |
| 5,170,666 A | 12/1992 | Larsen |
| 5,240,329 A | 8/1993 | Zinkosky |
| 6,277,771 B1 | 8/2001 | Nishimura et al. |
| 7,307,431 B2 | 12/2007 | Safai et al. |
| 7,385,392 B2 | 6/2008 | Schlicker et al. |
| 2003/0050557 A1* | 3/2003 | Susil ............. A61B 5/055 600/424 |

(Continued)

FOREIGN PATENT DOCUMENTS

CN        105823797 A    *  8/2016

OTHER PUBLICATIONS

Usamentiaga, R. et al., "Infrared Thermography for Temperature Measurement and Non-Destructive Testing", 2014, pp. 12305-12348.

(Continued)

*Primary Examiner* — Justin Seo
*Assistant Examiner* — John M Royston
(74) *Attorney, Agent, or Firm* — Marla Johnston; Brooks Kushman P.C.

(57) ABSTRACT

Systems and methods for conducting non-destructive testing of fiber composite components are disclosed. The system may include a wire coil proximate the component and a power source connected to the wire coil. A controller may be connected to the power source and configured to continuously vary a current passing through the wire coil to generate a constantly changing magnetic field. A temperature sensor may be configured to detect a temperature of a plurality of regions of the component. The power source may be an AC or DC power source. The method may include generating a constantly changing magnetic field in proximity to a carbon-fiber composite, thereby inducing an electrical current in the carbon-fiber composite, and measuring a temperature of a plurality of different regions of the carbon-fiber composite to determine whether a defect is present. A defect may be identified by a temperature abnormality in a region.

20 Claims, 2 Drawing Sheets

(56) References Cited

U.S. PATENT DOCUMENTS

| | | | |
|---|---|---|---|
| 2008/0022775 A1 | 1/2008 | Sathish et al. | |
| 2010/0156632 A1* | 6/2010 | Hyland | G08B 25/08 340/540 |
| 2012/0126803 A1* | 5/2012 | Goldfine | G01R 33/0064 324/239 |
| 2013/0235897 A1 | 9/2013 | Bouteyre et al. | |
| 2014/0176698 A1* | 6/2014 | Banerjee | G01N 21/21 348/92 |
| 2016/0065901 A1* | 3/2016 | Padate | G01J 5/08 348/143 |
| 2017/0328864 A1* | 11/2017 | Endou | G01N 27/9046 |

OTHER PUBLICATIONS

Pinto, F. et al., "In-situ damage detection in SMA reinforced CFRP", 2012, pp. 1-10.
Pinto, F. et al., "Multifunctional SMArt composite material for insitu NDT/SHM and de-icing", 2012, pp. 1-3, Abstract.
de Villoria, Roberto Guzmán et al., "Multi-physics damagesensing in nano-engineered structural composites." Nanotechnology, 2011, pp. 1-13.

\* cited by examiner

US 10,197,516 B2

NON-CONTACT QUALITY CONTROL OF FIBER COMPOSITES

TECHNICAL FIELD

The present disclosure relates to non-contact quality control of fiber composites, for example, carbon fiber composites.

BACKGROUND

Demands for greater fuel economy are increasing due to government legislation and customer preference. One approach to satisfying the increased fuel economy demand is reducing vehicle weight, for example, by increasing the usage of composite materials in the vehicle. Carbon fiber composites may provide the potential for significant weight reduction. However, current quality control systems for composites generally require the use of destructive test methods to ensure part performance. Moreover, in service repairs may require complete part replacement, as a definitive assessment of damage can prove challenging. A cost-effective non-destructive testing method may address some of these issues and facilitate additional inclusion of composite materials, such as carbon fiber composites.

SUMMARY

In at least one embodiment, a quality-control system for a fiber-composite component is provided. The system may include a wire coil proximate the component; a power source connected to the wire coil; a controller connected to the power source and configured to continuously vary a current passing through the wire coil to generate a constantly changing magnetic field; and a temperature sensor configured to detect a temperature of a plurality of regions of the component.

The power source may be an alternating current (AC) or a direct current (DC) power source. The temperature sensor may be a non-contact temperature sensor with respect to the component. In one embodiment, the non-contact temperature sensor is mounted to a robot arm and configured to scan a surface of the component. The system may include a processor configured to receive temperature data from the temperature sensor and configured to form a temperature map of the plurality of regions of the component. The processor may be further configured to generate an alert if at least one of the plurality of regions has a temperature that is above or below a threshold value.

In at least one embodiment, a method is provided. The method may include generating a constantly changing magnetic field in proximity to a carbon-fiber composite, thereby inducing an electrical current in the carbon-fiber composite; and measuring a temperature of a plurality of different regions of the carbon-fiber composite to determine whether a defect is present.

The constantly changing magnetic field may be generated by continuously changing a current through a wire coil. The current may be provided by an AC or DC power source. The measuring step may include using a non-contact temperature sensor to measure the temperature of the plurality of different regions of the carbon-fiber composite. In one embodiment, the non-contact temperature sensor is an infrared temperature sensor. The measuring step may include using a robotic arm having the non-contact temperature sensor attached thereto to scan the plurality of different regions of the carbon-fiber composite. The method may further include generating a temperature map of the plurality of different regions of the carbon-fiber composite. Determining whether a defect is present may include comparing the temperatures of the plurality of different regions and determining if at least one of the plurality of regions has a temperature that is above or below a threshold value.

In at least one embodiment, a method is provided. The method may include continuously changing a current through a wire coil to generate a constantly changing magnetic field in proximity to a carbon-fiber composite, thereby inducing an electrical current in the carbon-fiber composite; and measuring a temperature of a plurality of different regions of the carbon-fiber composite to determine whether a defect is present.

Determining whether a defect is present may include comparing the temperatures of the plurality of different regions and determining if at least one of the plurality of regions has a temperature that is above or below a threshold value. The method may include generating a temperature map of the plurality of different regions of the carbon-fiber composite. In one embodiment, the constantly changing magnetic field has a peak strength of at least 0.3 T at a surface of the carbon-fiber composite.

DETAILED DESCRIPTION

Figure 1:
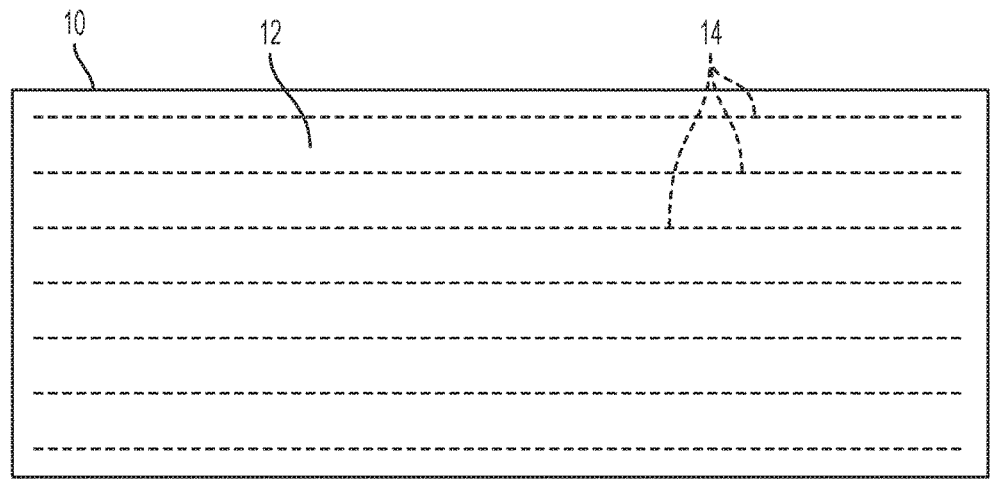
FIG. 1 is a schematic top view of a fiber composite, according to an embodiment.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As described above, current testing methods are typically destructive in nature. Routine destructive testing as a quality control method may pose a significant challenge to the use of fiber composites, such as carbon fiber composites, due to the high piece price costs of carbon fiber composites. Non-destructive testing may allow for fiber composite parts to be reused after testing, thereby providing significant cost savings.

However, current non-destructive inspection techniques are typically slow, limited in damage detection capability, labor intensive, or a combination thereof. These drawbacks may be an impediment to their use within the automotive industry for inspecting carbon fiber composites (e.g., due to the high volumes involved). A more rapid and autonomous inspection technique suitable for automotive composite components may facilitate increased use of fiber composites. The technique may be used by composite automotive component manufacturers, as well as automotive maintenance and repairers. The technique may be inexpensive, rapid, simple to use, and/or accurate, preferably all four.

There are multiple non-destructive techniques that could potentially be used to inspect automotive composites, such as tap testing, ultrasonics, X-ray radiography (e.g., computed tomography), thermography, acoustic emission, acousto-ultrasonics, magnetic resonance imaging, or vibrational NDE. However, each of these includes potential drawbacks for the inspection of composite components (e.g., carbon fiber composites). For example, each technique does not meet one or more of the following criteria: easy to operate; do not require extreme safety cautions; can be operated by non-technical personnel; ability to tolerate production environment—including dirt, noise, vibration etc.; robot automation available; potential to match manufacturing production cycle-times; available at an acceptable cost; or provide rapid, non-contact assessment.

Accordingly, in at least one embodiment, non-contact quality control techniques and systems for carrying out the technique are disclosed. The methods and systems may meet one or more of the criteria above, preferably most or all of them. Fiber composites generally include a resin and a plurality of fibers disposed within the resin. The fibers may be oriented in one or more directions (e.g., axial, perpendicular, 45°, etc.) or may be randomly oriented. The fibers may be relatively long (e.g., several inches or greater) or relatively short.

With reference to FIG. 1, a schematic top view of a fiber composite component 10 is shown, according to one example. The component 10 includes a resin matrix 12 and a plurality of fibers 14 embedded within the matrix 12. In the embodiment shown, the fibers 14 are long, axial fibers; however, the fibers 14 may have any orientation or length, as described above. The fibers 14 are referred to herein as carbon fibers, but other electrically conductive fibers may also be used. The fibers 14 may also be a combination of two or more types of conductive fibers. The resin matrix 12 may include any suitable resin for forming a fiber composite. Non-limiting examples of resins may include epoxies, polyesters, vinyl esters, polyethylene, polypropylene, TPO, PVA, BMI resin, or nylons. The resin may be a thermoset or a thermoplastic.

The component 10 may be a vehicle component, such as a deck or trunk lid, a door panel or other body panel, roof structure, instrument panel, pillars, hood, etc. However, the present disclosure is not limited to vehicle components. The component 10 may include at least one surface that will be visible in the finished vehicle, which may be referred to as a class-A surface. The surface of the component 10 is generally rich in resin matrix 12 and therefore not electrically conductive (e.g., high electrical resistance). Carbon fiber, on the other hand is more electrically conductive than the matrix 12. The electrical conductivity may depend on the quality of the carbon fiber. For example, carbon fiber may have an electrical conductivity of at least $1 \times 10^4$ S/m, $1 \times 10^5$ S/m, or $1 \times 10^6$ S/m. Because the surface of the component 10 is rich in resin matrix 12, to form a good contact connection to the fibers 14 the surface may need to be sanded or otherwise removed to expose the fibers 14. This may not be possible or acceptable for a class-A surface. Even for a non-class-A surface, if testing is to be performed on an assembled vehicle, the ends or the component may not be accessible to attach metal terminals.

Figure 2:
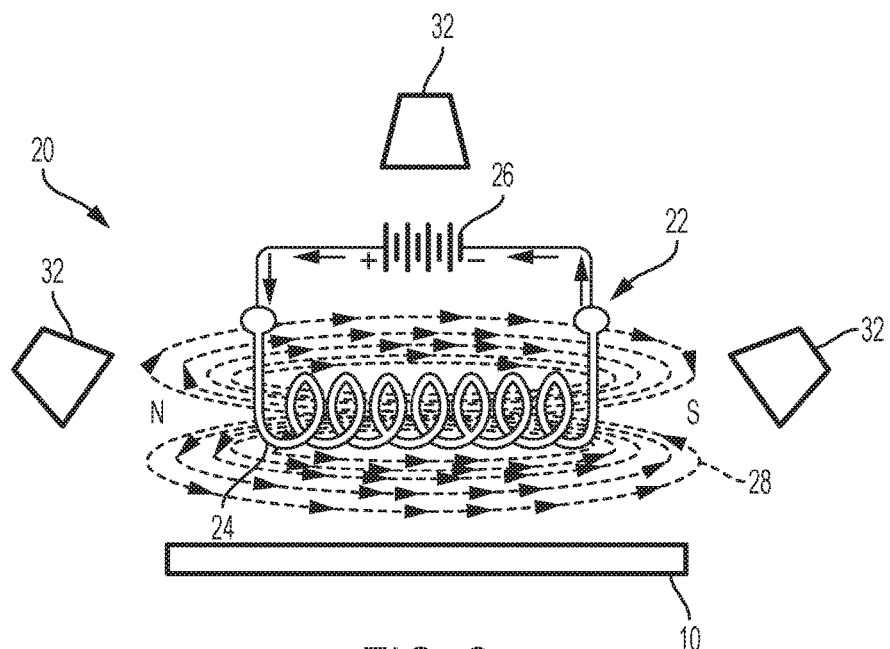
FIG. 2 is a schematic of a fiber composite defect-detection system, according to an embodiment.

Accordingly, with reference to FIG. 2, in at least one embodiment, non-contact quality control techniques and system are disclosed that do not require making physical contact or connections with the fibers 14 in the component 10. The system 20 may include a magnetic field source 22. In at least one embodiment, the magnetic field source 22 may be an electrical conductor 24, such as a wire, connected to a power source 26. The wire 24 may be in the shape of a coil, spiral or helix. When current is transmitted from the power source 26 through the wire 24, a magnetic field 28 is generated. This phenomenon is known in the art and will not be discussed in detail.

In one embodiment, the power source 26 may be an AC (alternating current) power source. AC is current in which the flow of electric charge periodically reverses direction, for example, in the shape of a sine wave or triangle wave. In another embodiment, the power source 26 may be a DC (direct current) power source. Since the current flow from an AC/DC power source may be constantly changing in a non-constant rate, the magnetic field that is generated from AC/DC current may also be constantly changing. This constantly changing magnetic field may be used to induce current in a nearby conductor, such as the carbon fibers 14 in the component 10.

In the embodiment shown, there is a single wire 24 connected to power source 26. The embodiment shown is schematic and not to scale. Any configuration of wire(s) 24 and power source(s) 26 may be used in order to create a changing magnetic field 28 that covers the entire component 10 with a strength sufficient to induce current in the fibers 14. There may be a single wire 24 that is large enough to generate such a changing magnetic field 28 or there may be multiple wires 24 arranged to generate the changing magnetic field.

In another embodiment, a moving magnetic field may be used to induce a current in the fibers 14. For example, a permanent magnet or an electromagnet (e.g., coil and power source) having a constant magnetic field may be moved to form a changing magnetic field. This changing magnetic field may induce current in the fibers 14 in a manner similar to the changing current approach described above.

Regardless of the mechanism of generating the changing magnetic field, the strength of the magnetic field may be sufficient to generate a meaningful or significant current in the fibers 14. For example, the magnetic field may be sufficient to generate a current in the fibers 14 capable of raising the average temperature of the composite component 10 at least 3° C. or at least 5° C. In one embodiment, the strength (e.g. peak strength or amplitude) of the magnetic field may be at least 0.3 tesla (T) at the surface of the composite component 10. For example, the he strength of the magnetic field may be at least 0.5 T, 1.0 T, 1.5 T, 2.0 T, or 2.5 T at the surface of the composite component 10.

Regardless of the mechanism used to generate it, the changing magnetic field may cause electric current flow in the conductive carbon fibers within the component. This may be similar to how Eddy currents are generated. As will be known to those of ordinary skill in the art, Eddy currents are circular electric currents induced within conductors by a changing magnetic field in the conductor, due to Faraday's law of induction. Eddy currents flow in closed loops within conductors, in planes perpendicular to the magnetic field. They can be induced within nearby stationary conductors by a time-varying magnetic field created by an AC electromagnet or transformer, for example, or by relative motion between a magnet and a nearby conductor. The magnitude of the current in a given loop is proportional to the strength of the magnetic field, the area of the loop, and the rate of change of flux, and inversely proportional to the resistivity of the material.

Figures 3, 4, 5:
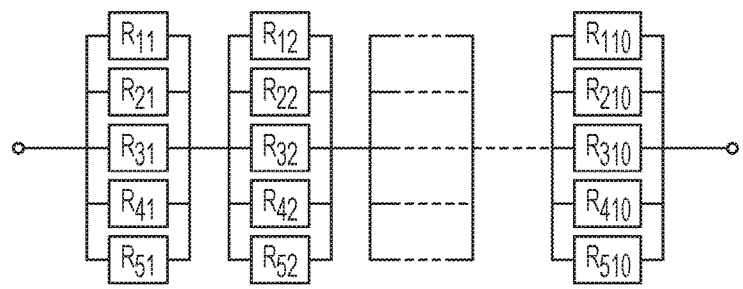
FIG. 3 is an example of a fiber composite separated into smaller regions representing a resistor, according to an embodiment.
FIG. 4 is a schematic diagramming the regions of FIG. 3 as an electrical circuit.
FIG. 5 is an example of a temperature map of a fiber composite that includes two regions having defects, according to an embodiment.

Once there is current flow in the carbon fibers, the carbon fiber composite will produce heat. The heat generation may be described by $$P = I^2 R = \frac{U^2}{R},$$

wherein P is the power of heat generation, I is the current, R is the resistance, and U is the voltage. With reference to FIG. 3, the component 10 of FIG. 1 may be divided into a plurality of smaller regions or areas 30 that may approximate a resistor. In the example shown, the component 10 is divided into a 10×5 grid (10 wide, 5 tall) for a total of 50 resistors. Each region 30 may be assigned a position within the grid, as shown. Each column of regions (e.g., $R_{11}$-$R_{51}$) may be treated as parallel resistors, as shown in FIG. 4.

For a fiber composite component having uniform fiber density and no defects, such as abnormal fiber density, fiber breakage, voids, foreign objects, delamination/debonding, or others, each region 30 can be expected to have the same resistance. However, if defects are present in a region, the resistance may change relative to the other regions. For example, if there is an abnormally high fiber content in the region, the resistance of the region may be decreased relative to the other regions, since the fibers (e.g., carbon fibers) are more conductive than the resin matrix. Alternatively, if there is an abnormally low fiber content in the region or the region includes voids or fiber breakage, the resistance of the region may be increased relative to the other regions. Regions having a higher resistance will have lower current flowing therethrough and therefore will generate less heat. In contrast, regions having lower resistance will have higher current flowing therethrough and therefore will generate more heat. In columns where there is a high resistance region, the other regions will have more current flowing therethrough and will therefore generate more heat than in a column having all uniform regions. Conversely, in columns where there is a low resistance region, the other regions will have less current flowing therethrough and will therefore generate less heat than in a column having all uniform regions.

Using the relationship U=IR, the heating power for each region (resistor) in a column (e.g., column 1) may be described by:

$$P11 = \frac{U11^2}{R11} = \frac{\left(I\frac{1}{\frac{1}{R11} + \frac{1}{R21} + \frac{1}{R31} + \frac{1}{R41} + \frac{1}{R51}}\right)^2}{R11}.$$

For example, if a constantly changing magnetic field capable of generating a current of 2 amps (A) is applied to the composite then a heating power can be calculated for each region. In this example, each region is assumed to have a resistance of 10 ohms, except for regions $R_{25}$ and $R_{35}$, which have resistances of 2 ohms and 20 ohms, respectively. Accordingly, region $R_{25}$ has a lower resistance than the standard regions (e.g., abnormally high fiber content) and region $R_{35}$ has a greater resistance than the standard regions (e.g., abnormally low fiber content, voids, breakage). Based on the equations above, the regions in each of the columns other than column 5 may generate 1.60 watts of heat. However, in column 5, the regions in rows 1, 4, and 5 may generate 0.55 watts while the regions in rows 2 and 3 may generate 2.77 watts and 0.28 watts, respectively. Accordingly, in column 5, the regions in row 3 may generate the least heat and the region in row 2 may generate the greatest heat, with the regions in rows 1, 4, and 5 in between.

Since the heat generated by defects is different compared to areas having uniform or "normal" fiber density, it has been discovered that the temperature of each region may be used to determine if a defect is present in a fiber composite. In at least one embodiment, the system 20 of FIG. 2 may be used to detect temperature differences in different regions of the component 10 and thereby identify regions having potential defects. The system 20 may include one or more non-contact temperature sensors 32 that are configured to measure the temperature of the component 10. The sensor(s) 32 may have a certain sensing area or spot size, for example, from 1 mm to 50 mm, or any sub-range therein, such as 5 to 25 mm or 5 to 15 mm. The sensing area may depend on the distance of the sensor from the component (e.g., working distance). For example, the spot size may decrease as the working distance increases. The spot size may correspond to the size of one region.

Accordingly, to analyze a fiber composite component 10, a constantly changing magnetic field 28 may be generated by a magnetic field source 22 in the vicinity of the component 10. The magnetic field 28 may be powerful enough to induce currents within the fibers 14 of the component 10. One or more non-contact temperature sensors 32 may measure the temperature of the component 10 while the magnetic field 28 is applied. In one embodiment, the temperature sensors 32 may be infrared temperature sensors. There may be a plurality of sensors 32 such that each sensor measures one region of the component (e.g., the spot size). Alternatively, the one or more non-contact temperature sensors 32 may move such that they measure the temperature of multiple regions (e.g., spot sizes) of the component 10. The one or more non-contact temperature sensors 32 may be mounted to a rail or guide and moved along the rail/guide to measure the entire component. Alternatively, the one or more non-contact temperature sensors 32 may be mounted to one or more robot arms and the arms may be moved along a programmed path to measure the entire component. While the temperature sensors 32 are shown as being on the same side of the component 10 as the magnetic field source 22 in FIG. 2, they may be on opposite sides (or in any other workable configuration). The one or more non-contact temperature sensors 32 may generate a temperature map 34 of the component showing the temperature of each region 30. In one embodiment, the one or more non-contact temperature sensors 32 may be connected to one or more computers, which may analyze data from the temperature sensors 32 and generate the temperature map 34.

With reference to FIG. 5 an example of a temperature map 34 is shown. Similar to the example above, the map 34 includes 50 regions 30 in a 10×5 grid. Each region 30 shows a temperature reading from a non-contact temperature sensor. In this example, the temperature sensor was a Fixed Infrared Temperature Transmitters from Omega with a spot size of 5 mm (at working distance of 100 mm) to 15 mm (working distance of 200 mm). A 3 amp (A) power supply was connected to the ends of the composite and used to simulate the current generated by a changing magnetic field. One 75 mm by 150 mm carbon fiber composite coupon was made to validate this technique. The sensor was mounted on a robot arm with a working distance of 100 mm. The robot was programmed to move along the sample with a speed of 15 mm/s. The first row was measured, then the sensor moved to the second row, and so forth until the whole composite was measured. The row spacing and column spacing were 15 mm. The total scanning time was around 50 seconds. The data from the temperature sensor was sent to a computer, which generated the temperature map of FIG. 5.

The region $R_{22}$ (row 2, column 2) was purposefully made with lower carbon fiber content (20%) and region $R_{38}$ (row 3, column 8) was purposefully made higher carbon fiber content (60%) (mass fraction), while the other regions were made with a carbon fiber content of 40%. Accordingly, $R_{22}$ has a higher resistance and $R_{38}$ has a lower resistance than the other regions. As shown in the temperature map 34 in FIG. 5, the regions in columns 1, 3-7, and 9-10 (the unaltered columns) all have a temperature of 35° C., with a couple at 34° C. In column 2, $R_{22}$ has a significantly lower temperature (29° C.) compared to the other regions in column 2 (46-47° C.), which in turn are at a higher temperature than the unaltered columns (~35° C.). In column 8, $R_{38}$ has a significantly higher temperature (39° C.) compared to the other regions in column 8 (32° C.), which in turn are at a lower temperature than the unaltered columns (~35° C.).

Accordingly, this sample data confirms that defects such as variations in fiber content can be detected in a non-destructive manner using non-contact temperature sensors. The data closely corresponds to the mathematical approximation described above. In addition to being non-destructive and non-contact, the technique satisfies most, if not all, of the criteria disclosed above. The technique is easy to operate and does not require extreme safety cautions. The technique can likely be operated by non-technical personnel and can be automated (e.g., using robots). It is able to tolerate a vehicle production environment, including dirt, noise, vibration, etc., since it is non-contact and relies on temperature readings. The technique is relatively fast and has the potential to match manufacturing production cycle-times. The equipment for the system is relatively inexpensive and can be implemented in a cost-effective manner.

The data generated for the temperature map 34 in FIG. 5 is an example and the temperatures therein and the experimental parameters are not intended to be limiting. The component to be tested may have any size and/or shape. The component may be a vehicle component such as a trunk or deck lid, door panel, or other component. The component may be attached or otherwise coupled to other components of the vehicle during the analysis. For example, the system 20 may be incorporated into the assembly process such that components of a partially or completely assembled vehicle may be tested. There may be a single non-contact temperature sensor or a plurality of sensors. The number of sensors may depend on the size of the component being analyzed and/or the desired total scanning time. The component may be relatively flat or may have a complex geometry. The temperature sensors may be attached to a robot arm that is programmed to maintain a certain working distance from the surface of the component.

In one embodiment, the temperature sensors and the magnetic field source may be connected (directly or indirectly) to a computer or computer network. The computer(s) may control and be programmed to generate the constantly changing magnetic field and to receive temperature data from the temperature sensors. The computer(s) may further be programmed to analyze the data and generate a temperature map, such as the map shown in FIG. 5. The computer(s) may be programmed to identify regions that are above or below an average temperature or a predetermined target temperature by a certain tolerance or threshold value. For example, the computer may be programmed to detect and/or identify regions that are at least 3° C. below or above the average or predetermined target temperature. The tolerance or threshold may vary depending on the desired uniformity of the composite, the strength of the magnetic field, or other factors. In one embodiment, the threshold may be at least 2, 3, 4, or 5° C. The computer(s) may be further programmed to generate an alert or alarm if one or more regions are above/below the target temperature. For example, an audible and/or visual alarm may be triggered and/or a production line may be stopped. Similar to the temperature tolerance, the number of identified out-of-specification regions that are needed to trigger the alarm/alert may depend on the desired uniformity of the composite or other factors.

In addition to, or instead of, using the above disclosed technique and system, surface resistivity or resistance may be used to analyze a fiber composite component for defects. Surface resistance may be defined as a ratio of voltage to current flowing between two electrodes that are in contact with a surface. Surface resistivity may be defined as a ratio of voltage drop per unit length to the current per unit width. A surface resistance/resistivity meter may include a probe having two electrodes. The meter may provide a constant voltage to the electrodes and measure the current flowing therebetween. Based on the configuration of the electrodes, the meter may then calculate both surface resistance and surface resistivity. Different electrode configurations may be used. In one example, the electrodes may be concentric rings. In another example, there may be more than two electrodes, such as four electrodes.

As described above, defects may affect the resistance of a fiber composite. Therefore, a surface resistance/resistivity meter and probe may be able to detect differences in resistance at different regions in the composite. Similar to the magnetic inductance technique, the component may be divided into multiple regions and the surface of each region may be tested using the resistance meter. The resistance values of regions with uniform or "normal" fiber loading should be relatively consistent, while regions having defects may have higher or lower resistances, depending on the defect type.

The surface of the fiber composite component may be relatively resin-rich compared to the bulk of the component. Accordingly, in some circumstances, the surface resistance measurement tool may have difficulty distinguishing between areas including defects and those without. In one embodiment, the probe of the tool may include a projection configured to pierce the surface of the composite in order to analyze the composite at a depth below the surface. This measurement may allow the tool to analyze a region of the component that is closer to the bulk and is likely to have a greater concentration of fibers. The projection may be very small, such that the hole or opening created is not visible or barely visible when the probe is removed.

In one embodiment, the surface resistance/resistivity technique may be used independently to determine potential defects in a component. In another embodiment, the surface resistance/resistivity technique may be used in combination with the temperature sensing technique described above. For example, the temperature sensing technique may be applied to some or all components moving down an assembly line. A system similar to that of FIG. 2 may be implemented and automated to test the components. If a component is analyzed by the system and one or more regions are detected to have a temperature above/below the threshold, the component may be identified for additional testing. The component may then be tested using the surface resistance/resistivity technique to confirm or double-check the findings from the magnetic inductance system. For example, only the regions identified by the previous system may be analyzed or the entire component may be tested. Similarly, the surface resistance/resistivity technique could be used to calibrate or test the magnetic inductance system, or vice versa. Of course, the reverse of the above approach could also be implemented, where components are first tested using the surface resistance/resistivity technique and then the analysis may be confirmed or double-checked by the magnetic inductance system.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A quality-control system for a fiber-composite component having fibers axially aligned along a longitudinal axis of the composite, comprising:
    a wire helix wound around a helix axis and proximate the component such that the helix axis and longitudinal axis are aligned;
    a power source connected to the wire helix;
    a controller connected to the power source and configured to continuously vary a current passing through the wire helix to generate a constantly changing magnetic field;
    a temperature sensor configured to detect a temperature of regions of the component; and
    a processor configured to receive temperature data from the temperature sensor and configured to form a temperature map of the regions of the component and to generate an alert in response to at least one of the regions having a temperature that is above or below a threshold value.

2. The system of claim 1, wherein the power source is an alternating current (AC) power source.

3. The system of claim 1, wherein the power source is a direct current (DC) power source.

4. The system of claim 1, wherein the temperature sensor is a non-contact temperature sensor with respect to the component.

5. The system of claim 4, wherein the non-contact temperature sensor is mounted to a robot arm and configured to scan a surface of the component.

6. The system of claim 1, wherein the processor is further configured to generate an alert in response to a threshold value of a number of the regions having a temperature that is above or below a threshold value.

7. The system of claim 1, wherein the temperature sensor is arranged on a side of the component opposite the wire helix.

8. A method, comprising:
    aligning a helix axis of a wire helix with a longitudinal axis of a carbon-fiber composite having fibers axially aligned along the longitudinal axis;
    generating a constantly changing magnetic field through the wire helix in proximity to the composite to induce an electrical current therein; and
    measuring a temperature of different regions of the composite to determine whether a defect is present.

9. The method of claim 8, wherein the measuring step is performed by a temperature sensor arranged on a side of the component opposite the wire helix.

10. The method of claim 8, wherein the current is provided by an AC power source.

11. The method of claim 8, wherein the current is provided by a DC power source.

12. The method of claim 8, wherein the measuring step includes using a non-contact temperature sensor to measure the temperature of the different regions of the carbon-fiber composite.

13. The method of claim 12, wherein the non-contact temperature sensor is an infrared temperature sensor.

14. The method of claim 12, wherein the measuring step includes using a robotic arm having the non-contact temperature sensor attached thereto to scan the plurality of different regions of the carbon-fiber composite.

15. The method of claim 8, further comprising generating a temperature map of the different regions of the carbon-fiber composite.

16. The method of claim 8, wherein determining whether a defect is present includes comparing the temperatures of the different regions and determining if at least one of the regions has a temperature that is above or below a threshold value.

17. A method, comprising:
    aligning a helix axis of a wire helix with a longitudinal axis of a carbon-fiber composite having fibers axially aligned along the longitudinal axis;
    continuously changing a current through the wire helix to generate a constantly changing magnetic field in proximity to the carbon-fiber composite to induce an electrical current therein; and
    measuring a temperature of different regions of the carbon-fiber composite to determine whether a defect is present.

18. The method of claim 17, wherein determining whether a defect is present includes comparing the temperatures of the different regions and determining if at least one of the regions has a temperature that is above or below a threshold value.

19. The method of claim 17, further comprising generating a temperature map of the different regions of the carbon-fiber composite.

20. The method of claim 17, wherein the constantly changing magnetic field has a peak strength of at least 0.3 T at a surface of the carbon-fiber composite.

* * * * *